United States Patent
Fischer et al.

(10) Patent No.: US 7,137,965 B2
(45) Date of Patent: Nov. 21, 2006

(54) DEVICE FOR THE IONTOPHORETIC DELIVERY OF A DRUG

(75) Inventors: Gregory A. Fischer, Salt Lake City, UT (US); Malcolm E. Taylor, Pepperell, MA (US); Edward M. Kolvek, West Newbury, MA (US)

(73) Assignee: Iomed, Inc., Salt Lake City, UT (US)

( * ) Notice: Subject to any disclaimer, the term of this patent is extended or adjusted under 35 U.S.C. 154(b) by 918 days.

(21) Appl. No.: 10/054,713

(22) Filed: Jan. 22, 2002

(65) Prior Publication Data

US 2003/0060798 A1 Mar. 27, 2003

Related U.S. Application Data (63) Continuation of application No. 09/960,833, filed on Sep. 21, 2001, now Pat. No. 6,953,446.

(51) Int. Cl.
*A61N 1/30* (2006.01)

(52) U.S. Cl. .................. 604/93.01; 604/20; 220/265
(58) Field of Classification Search ............. 604/19, 604/48, 93.01, 410, 403, 408, 411, 415; 222/82, 222/83; 206/207; 220/265

See application file for complete search history.

(56) References Cited

U.S. PATENT DOCUMENTS

| 4,258,863 A | * | 3/1981 | Ness ........................... 222/83 |
| 5,310,404 A | | 5/1994 | Gyory et al. ................. 604/20 |
| 5,320,598 A | | 6/1994 | Haak et al. ................... 604/20 |
| 5,377,874 A | * | 1/1995 | Brown ......................... 222/82 |
| 5,582,587 A | | 12/1996 | Gyory et al. ................. 604/20 |
| 5,830,193 A | * | 11/1998 | Higashikawa ............... 604/191 |

* cited by examiner

*Primary Examiner*—LoAn H. Thanh
(74) *Attorney, Agent, or Firm*—Factor & Lake (57) ABSTRACT

An iontophoretic drug delivery device storage apparatus and a method of using that device is disclosed. The device comprises a fluid reservoir, an electrode assembly and a tray apparatus. The fluid reservoir is capable of retaining a medicament and has a sealed fluid chamber defined by at least one seal. The seal includes a weaker region and a pinch-like configuration associated with that region such that application of pressure to the fluid reservoir breaks the weaker region of the seal, releasing the retained medicament. The electrode assembly comprises an active electrode, at least two passive electrodes a medicament carrying region, and a moat region around the medicament carrying region so that once fluid is delivered from the fluid reservoir to the electrode assembly the fluid is substantially retained in the medicament carrying means.

6 Claims, 4 Drawing Sheets

DEVICE FOR THE IONTOPHORETIC DELIVERY OF A DRUG

RELATED APPLICATIONS

This application is a continuation of application Ser. No. 09/960,833 now U.S. Pat. No. 6,953,446, filed Sep. 21, 2001, and entitled Method and Device for the Iontophoretic Delivery of a Drug; the content of which is expressly incorporated by reference herein.

BACKGROUND OF THE INVENTION

1. Field of the Invention

The present invention relates in general to drug delivery devices used to deliver ionic medicaments through the skin or other tissues, and, more particularly, to fluid assemblies and electrode assemblies for the release and delivery of a medicament to a patient.

2. Background Art

Drug delivery devices have been known in the art for a number of years. Furthermore, drug delivery devices having fluid delivery assemblies for delivering fluid to bioelectrodes are likewise well known. Conventional fluid delivery assemblies have utilized a number of methods for the release and delivery of a fluid. These methods include rupturing one or more pouches contained within a rigid or semi-rigid container, or having a number of microcapsules within a porous membrane that, when ruptured, release a fluid through the membrane. These methods include a number of drawbacks, including the necessity for several separate structures, and the additional and sometimes cumbersome structures necessary to direct the flow of the released fluid.

Iontophoretic drug delivery devices, a subset of drug delivery devices, have also been known in the art for some time. These devices provide the electromotive force that drives an ionic drug from a pad or sponge containing the drug through the skin or other surface of a patient. Conventional drug delivery devices generally include a single active electrode and a single passive electrode, completing the circuit once the two are attached to the tissue of a patient. However, this electrode alignment has the drawback of requiring either high electric fields to deliver sufficient drug to the area, resulting in unwanted sensation and burning, or lower electric fields and resultantly lower delivery rates of the drug. Therefore, the use of a single set of an active and a passive electrode often results in unwanted electric field concentration or in decreased electrode performance.

The conventional iontophoretic devices additionally utilize well known methods of retaining a medicament in the drug delivery device, including gel sponges and disbursement pads. These media retain a medicament until placed next to skin/tissue and subjected to an electric current. However, these media can leak or seep fluid once applied, causing a short-circuit of the entire device.

It is therefore an object of the present invention to provide a simple and effective means for releasing a fluid from a reservoir, and then directing the flow of that fluid in a predetermined direction.

It is a further object of the present invention to provide consistent and optimum iontophoretic delivery of a drug while minimizing the negative effects of a concentrated electric field.

It is additionally an object of the present invention to provide a simple and effective structure for the prevention of migration of the medicament in the device out of the delivery pad towards the passive electrode.

It is also an object of the present invention to provide an integrated device and method, utilizing the above advantages, for the delivery of a fluid to a drug delivery device, and then to the tissue of a patient, while maintaining the integrity of the electrodes and the medicament.

These and other objects of the invention will be apparent to those having ordinary skill in the art in light of the associated specification, claims and drawings.

SUMMARY OF THE INVENTION

The present invention is directed to a fluid reservoir for use with a drug delivery device. The fluid reservoir has a sealed fluid chamber having a top surface and a bottom surface, and a cavity therebetween. The cavity is at least partially defined by at least one seal. The cavity serves to house a fluid therewithin. The invention further includes means for fracturing at least a portion of the at least one seal, and, means for controllably releasing a liquid, positionable within the cavity, out of the cavity.

In another preferred embodiment, the at least one seal comprises a first seal and a second seal, further defining the cavity therebetween, and, the fracturing means is associated with the first seal. The fluid reservoir may be oval in shape, and the first and second seals are concentric with one another. However, it is contemplated that the fluid reservoir be configured in numerous geometrical patterns, such as circles, rectangles, and squares.

In yet another preferred embodiment, one of the top and bottom surfaces of the fluid reservoir includes means for directing released fluid to a region adjacent the fluid reservoir, wherein the directing means comprises at least one slit in the associated top or bottom surface. Additionally, at least a portion of the top surface of the fluid reservoir is deformable upon exertion of a force.

In still another preferred embodiment, at least one seal comprises at least a first region of attachment and a second region of attachment. The fracturing means comprises the first region of attachment having a weaker attachment than the second region of attachment.

In another preferred embodiment, the control means comprises at least a portion of the seal having a pinch-like configuration.

This present invention is also directed to an electrode assembly for use with a drug delivery device. The electrode assembly comprises means for carrying a medicament; an active electrode in electrical communication with the carrying means; at least two passive electrodes; and means for securing the electrode assembly to a surface of a patient. Upon securement, the active electrode is distally spaced from the at least two passive electrodes, and the at least two passive electrodes are distally spaced from each other.

In such a preferred embodiment of the invention, the at least two passive electrodes are spaced on opposite sides of the active electrode, relative to one another. The medicament carrying means may comprise a dispersive pad, such as a gel sponge.

In another preferred embodiment, the electrode assembly further includes a medicament migration barrier region adjacent the medicament carrying means. The medicament migration barrier may be spaced from the dispersive pad, creating a moat-like region therebetween.

In another preferred embodiment, the electrode assembly further comprises a separator pad having a surface, and the securing means comprises at least a portion of the surface of the separator pad having an adhesive. The separator pad may additionally comprise means for preventing migration of a medicament. The separator pad may be positioned adjacent the active electrode and at least one of the at least two passive electrodes.

In a preferred embodiment, the securing means comprises an electrically conductive adhesive attached to the at least two passive electrodes. Such an adhesive may comprise Gum Karaya.

In another embodiment, the electrode assembly comprises at least one fluid reservoir capable of retaining a medicament, and an assembly tray. The assembly tray is configured to hold the electrode assembly and the at least one fluid reservoir. The assembly tray comprises a substantially rigid surface which is capable of deformation upon application of a force.

In such a preferred embodiment the at least one fluid reservoir comprises at least two fluid reservoirs.

The present invention is also directed to an electrode assembly for use with a drug delivery device, comprising means for carrying a medicament; means for preventing the migration of a medicament spaced from the carrying means, creating a moat region therebetween; an active electrode in electrical communication with the carrying means; at least one passive electrode; and means for securing the electrode assembly to a surface of a patient.

In another embodiment, the invention includes at least two passive electrodes. Preferably, the securing means secures the electrode to a surface of a patient with the active electrode distally spaced from the at least two passive electrodes, and the at least two passive electrodes are distally spaced from one another.

The invention also discloses an electrode assembly for use with a drug delivery device, comprising means for carrying a medicament; an active electrode, in electrical communication with the carrying means, comprising a silver conductive element; at least one passive electrode, comprising a carbon conductive element; and means for securing the electrode assembly to a surface of a patient. Preferably, the at least one passive electrode comprises at least two passive electrodes. It is also preferred that at least two passive electrodes are spaced on opposite sides of the active electrode, relative to one another.

In another embodiment of the invention, the electrode assembly further comprises a fluid reservoir capable of retaining a medicament, and an assembly tray. The assembly tray is configured to hold the electrode assembly and the fluid reservoir, and comprises a substantially rigid surface. The rigid surface is capable of deformation upon application of a force.

The present invention additionally discloses an iontophoretic drug delivery apparatus, comprising a fluid reservoir capable of retaining a medicament. The fluid reservoir comprises a sealed fluid chamber having a top surface and a bottom surface, and a cavity therebetween, the cavity being at least partially defined by at least one seal. The cavity serves to house a fluid therewithin. The apparatus also includes means associated with the sealed fluid chamber for enabling release of a fluid therefrom; and, means for controllably releasing a liquid, positionable within the cavity, out of the cavity. An electrode assembly is associated with the fluid reservoir and comprises means for carrying a medicament; an active electrode in electrical communication with the carrying means; at least two passive electrodes; means for preventing the migration of a medicament, adjacent the active electrode and the at least two passive electrodes, spaced from the active electrode (so as to create a moat-like region therebetween) and, means for securing the electrode assembly to a surface of a patient, wherein upon securement the active electrode is distally spaced from the at least two passive electrodes, and the at least two passive electrodes distally spaced from each other. A tray assembly is configured to hold both the fluid reservoir and the electrode assembly in their relative positions. The tray assembly comprises a substantially rigid surface, capable of deformation upon application of a force. Furthermore, the apparatus includes means for storing the completed assembly.

The invention also discloses a method for releasing a fluid from a fluid reservoir. The method comprises the steps of a) depressing at least a portion of a sealed fluid chamber, wherein the fluid chamber includes a cavity at least partially defined by at least one seal, having a fluid therewithin; b) fracturing at least a portion of the at least one seal; and, c) controllably releasing the fluid out of the cavity.

The fluid chamber may additionally comprise a top surface and a bottom surface. Accordingly, the step of depressing comprises deforming at least a portion of the top surface.

In a preferred embodiment of the invention, the at least one seal comprises a first seal and a second seal, and the step of fracturing at least one seal comprises the step of fracturing the first seal. It is contemplated that the at least one seal have a pinch-like configuration.

In yet an additional embodiment of the invention, the at least one seal comprises a first region of attachment and a second region of attachment and the step of fracturing comprising fracturing at least a portion of the first region of attachment.

The present invention is further directed to a method for iontophoretically administering a medicament to a patient using an electrode assembly. The method comprises the steps of a) impregnating a means for carrying a medicament, associated with an electrode assembly, with a medicament; and b) applying the electrode assembly to a surface of a patient, wherein the electrode assembly comprises an active electrode and at least two passive electrodes. The step of applying comprises the steps of c) placing the active electrode in distally spaced relation to the at least two passive electrodes, and placing the at least two passive electrodes in distally spaced relation to one another; and d) applying an electrical potential across the active electrode, the surface of the skin, and the at least two passive electrodes in such a way so as to drive the impregnated medicament from the carrying means and into the skin.

The invention still further discloses a method for iontophoretically applying a medicament to a patient, comprising the steps of a) applying a force to a top surface of a fluid reservoir, associated with an electrode assembly, the fluid reservoir having a cavity and a fluid contained therein; b) compressing at least a portion of the top surface of the fluid reservoir; c) fracturing at least a portion of a first region of at least one seal of the fluid reservoir while substantially maintaining the integrity of a second region of the at least one seal; d) releasing the fluid from the cavity within the fluid reservoir; e) directing the flow of the released fluid, out of the cavity, and onto a medicament carrying means; and, f)iontophoretically administering the medicament to a patient using the electrode assembly.

Additionally, the invention is also directed to a method for iontophoretically applying a stored medicament to a patient, comprising the steps of a) removing a tray assembly from storage, the tray assembly comprising a substantially rigid shell, configured to hold a fluid reservoir and an electrode assembly in relative positions, and a removable cover; b) applying force to a portion of the shell, associated with the fluid reservoir; c) compressing at least a portion of the shell into a top surface of the fluid reservoir; d) fracturing at least a portion of a first region of at least one seal of the fluid reservoir, while substantially maintaining the integrity of a second region of the at least one seal; e) releasing a fluid from a cavity within the fluid reservoir; f) directing the flow of a released fluid out of the cavity, and onto a medicament carrying means, a part of the electrode assembly; g) removing the electrode assembly from the tray assembly; h) applying the electrode assembly to a surface of a patient, wherein the step of applying further comprises placing an active electrode, in electrical communication with the medicament carrying means, in distally spaced relation to at least two passive electrodes; i) placing the at least two passive electrodes in distally spaced relation to one another; and j) iontophoretically administering the fluid to a patient using the electrode assembly.

BEST MODE OF THE INVENTION

Figure 1:
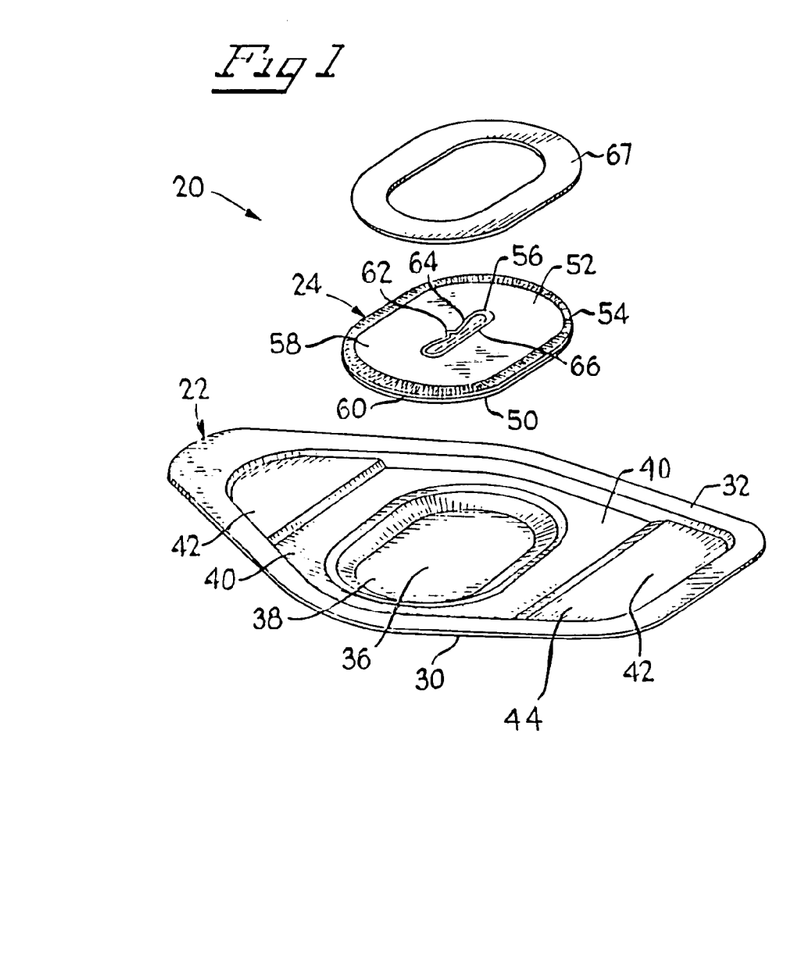
FIG. 1 of the drawings is an exploded view of the tray assembly and the pouch assembly.
Figure 2:
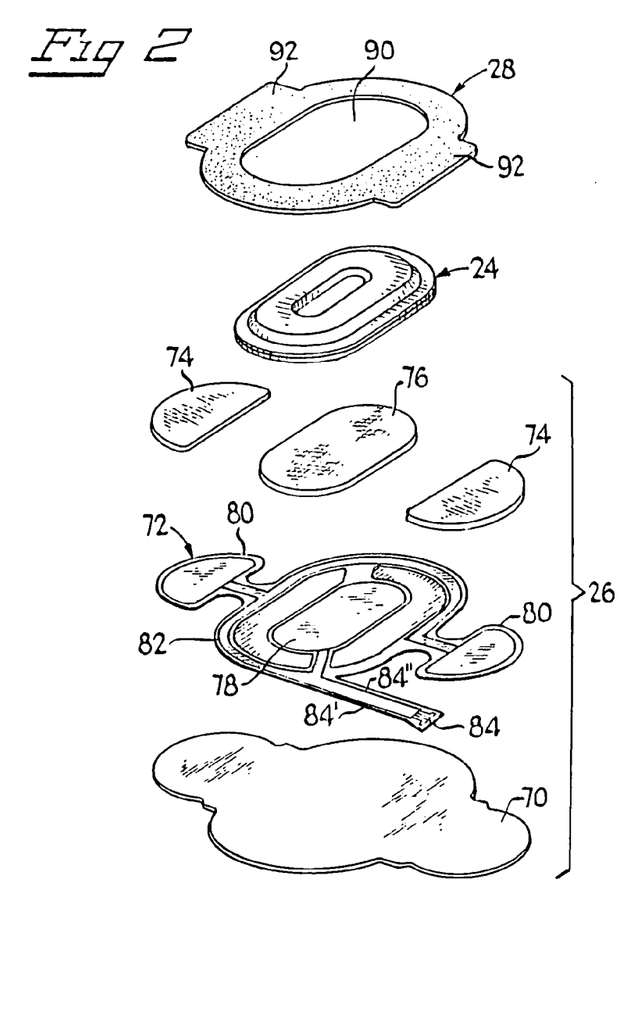
FIG. 2 of the drawings is an exploded view of the electrode assembly and the separator pad.

Referring now to FIGS. 1 and 2, iontophoretic drug delivery device storage apparatus 20 is shown as comprising tray assembly 22, pouch assembly 24, separator pad 28 and electrode assembly 26. When properly assembled, storage apparatus 20 enables the secure and safe storage, transportation, and handling of the enclosed items. Additionally, and as will be discussed further below, once tray assembly 22 is opened, electrode assembly 26 can be removed, and operatively placed upon a patient for the iontophoretic administration of a medicament.

Figure 6:
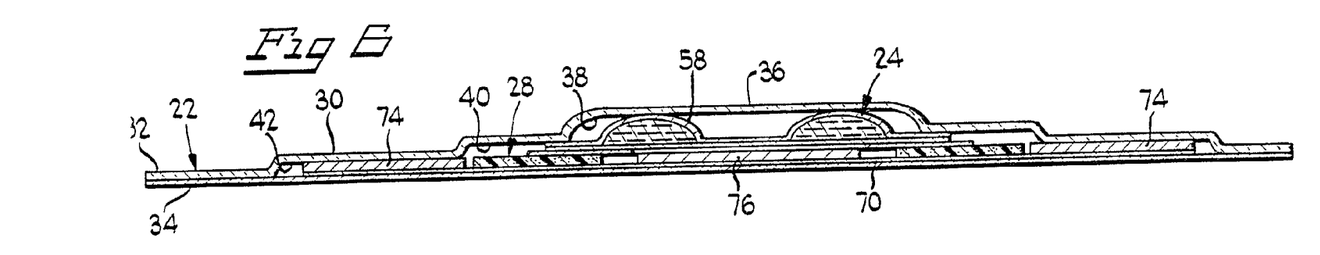
FIG. 6 of the drawings is a longitudinal cross-sectional view of the storage device.
Figure 7:
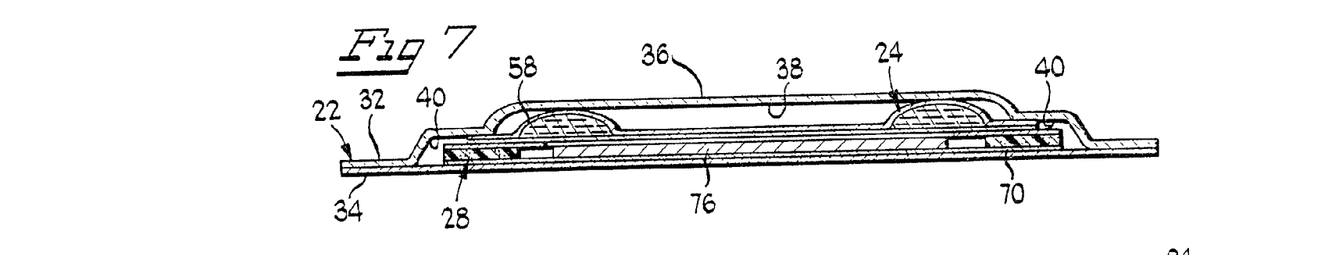
FIG. 7 of the drawings is a transverse cross-sectional view of the storage device.

Tray assembly 22 is shown in FIG. 6 as comprising outer shell 30 having three distinct recessed areas, first recess 38, second recess 40, and third recess 42. These recessed areas are configured so as to enable the secure insertion and containment of pouch assembly 24, separator pad 28, and electrode assembly 26 in their relative positions. First recess 38, relatively the deepest of the three, is configured in substantially the same shape as pouch assembly 24. Second recess 40, the middle section, is configured relatively wider than first recess 38. It is configured specifically so as to receive separator pad 28, and to hold that member in a secure position relative to pouch assembly 24. The third and final recessed area is the shallowest of the three. It is the broadest recessed area, and preferably runs nearly the entire length of outer shell 30. Third recess 42 is configured to receive and hold electrode assembly 26. As will be discussed further, third recess 42 additionally includes extended area 44, as can best be seen in FIG. 4. This area provides a storage location for lead wires 84 of electrode assembly 26.

Although the above discussion is focused on outer shell 30 having a specified number of recessed areas for insertion of the three components, it is additionally contemplated that other configurations could accomplish the same functions of secure retention of the elements in their appropriate relative positions, while not deviating from the ideas disclosed within this application. For example, outer shell 30 could have only one or two recessed areas, with the various components being configured to maintain proper alignment within tray assembly 22. Additionally, it is also contemplated that more than three recessed areas are acceptable, as would be contemplated by one of ordinary skill in the art.

Figure 3:
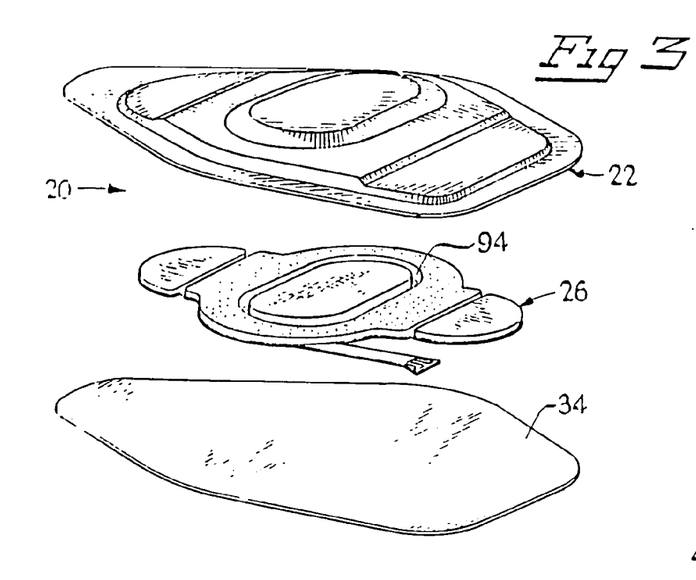
FIG. 3 of the drawings is an exploded view of the iontophoretic drug delivery device storage device before sealing.

Preferably, and as can be seen in FIG. 1, outer shell 30 additionally includes rim 32 along the circumference of the upper portion of tray assembly 22 and adjacent third recess 42. Rim 32 is configured to provide an area of attachment for cover 34 (shown in FIG. 3). In final, preferred form, pouch assembly 24, separator pad 28, and electrode assembly 26 are all inserted into their relative locations in tray assembly 22, and, thereafter, cover 34 is attached to rim 32, sealing iontophoretic device therein for safe and secure storage and handling.

Outer shell 30 of tray assembly 22 additionally aids in the safe and secure storage and handling of pouch assembly 24, separator pad 28, and electrode assembly 26. In order to do so, outer shell 30 is preferably constructed from a rigid or semi-rigid material to protect the retained contents. This rigid or semi-rigid material is preferably a plastic material, such as polypropylene, but may be constructed from any number of similar materials known in the art.

Additionally, the rigid to semi-rigid outer shell 30 of tray assembly 22 should include at least a portion 36 that is deformable upon the application of a force. Generally, outer shell 30 may be formed from a material that is substantially inflexible to the application of force. However, it is necessary that outer shell 30 have at least a portion that is capable of deformation upon application of a force. Deformable portion 36 may be constructed from the same material as the rest of the shell, with a lesser cross-linking density, or deformable portion 36 may even be constructed from a different material altogether. In any case, deformable portion 36 of outer shell 30 must allow for deformation of the shell upon application of a predetermined force.

Deformable portion 36 may be included on any number of places on outer shell 30. For example, the portion 36 may be a part of the entire outer shell 30, or may include only sections of the entire outer shell. Preferably, deformable portion 36 of outer shell 30 may be associated with only the first recessed area, corresponding substantially with the shape of the pouch assembly 24. This configuration provides for the functionality of being able to compress outer shell 30 at or around the inserted pouch assembly 24, and still provides for the protection of the remainder of the components of storage device 20, such as pouch assembly 24, electrode assembly 26, and separator pad 28.

Pouch assembly 24 is shown in FIG. 1 prior to insertion into tray assembly 22. Pouch assembly 24 comprises top surface 50, bottom surface 52, outer seal 54, and inner seal 56. Top surface 50 and bottom surface 52 are connected at both the outer seal 54 and inner seal 56 to create sealed fluid chamber 58. Sealed fluid chamber 58 is capable of holding a liquid, gel, or other fluidic material for later release.

Figure 10:
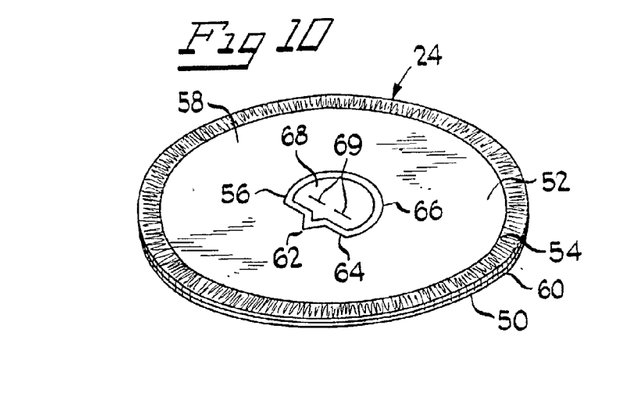
FIG. 10 of the drawings is a perspective view of an alternative design of the pouch assembly.
Figure 11:
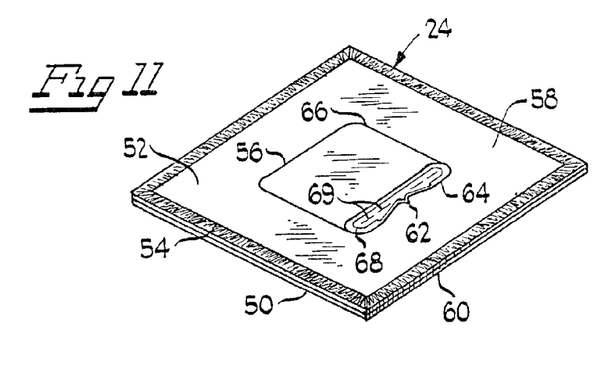
FIG. 11 of the drawings is a perspective plan view of an alternative design of the pouch assembly.

As pictured, pouch assembly 24 is shaped in a generally oval shape. Alternative configurations can be seen in FIGS. 10 and 11, showing pouch assembly 24 as generally circular and generally square. Any number of pouch configurations are similarly possible for pouch assembly 24, as would be readily understood by one of ordinary skill in the art.

Top 50 and bottom 52 surfaces of pouch assembly 24 are preferably made of an inexpensive, non-reactive, and easily formable material, such as aluminum. The choice of material allows for the top 50 and bottom 52 surfaces to be substantially non-reactive with whatever fluid is contained within sealed fluid chamber 58, while still allowing any number of choices with respect to the shape and configuration of pouch assembly 24. The material chosen should, however, be resistant to minor applications of force. In order to maintain the integrity of pouch assembly 24 over periods of time, including periods of time where pouch assembly 24 may be stored in a stacked configuration, pouch assembly 24 should not burst unless directed and intentional force is applied to at least one of the top 50 or bottom 52 surfaces.

Additionally, it is necessary to ensure that the material selected for top surface 50 and bottom surface 52 be non-reactive with the fluid to be contained in fluid chamber 58. In order to do so, it is preferable to use a coated material. For example, if aluminum is selected as the material for the top and bottom surfaces of pouch assembly 24, it is preferable to coat the material with a protective coating such as an ethylene ionomer. Specifically, the preferred material for the top and bottom surfaces comprise a thin layer of aluminum coated with a small amount of Surlyn™ sealant, an ethylene ionomer. With this configuration, the pouch material is thin, durable, non-reactive and relatively inexpensive.

Top surface 50 additionally comprises depressable area 60. Depressable area 60 is deformable upon application of a force. Preferably, force is applied to depressable area 60 in the direction of bottom surface 52, deforming top surface 50 towards bottom surface 52, and placing force upon the fluid contained within the sealed fluid chamber 58.

Depressable area 60 preferably coincides with the entire top surface 50 of pouch assembly 24, allowing force application at any point along the surface to transfer force into the fluid itself. Additionally, a smaller area of top surface 50 may be depressable, with the rest of the top surface remaining rigid or semi-rigid. The area of depressability is arbitrary, in fact, except for that some area of top surface 50 must be capable of deformation.

Similarly, and as would be obvious to one having ordinary skill in the art, bottom surface 52 may have one or more areas that are depressable. In that case, application of force to depressable area 60 of bottom surface 52 would deform bottom surface 52 in the direction of top surface 50, placing a force upon the fluid contained in sealed fluid chamber 58.

Top and bottom surfaces 50, 52, respectively, are connected at outer and inner seals, 54, 56, respectively, so as to seal fluid chamber 58 between the top and bottom surfaces. The outer and inner seals, 54, 56, are preferably created through standard welding techniques, by placing the top and bottom surfaces next to one another, and applying directed pressure or heat at the desired seal location. Thus, the top and bottom surfaces are unitized at that point.

It is also contemplated, however, that an additional substance could be used to seal the top and bottom surfaces together. For example, an adhesive or a stitching process can be used which would render the area between the top and bottom surfaces sealed. Preferably, however, any additional substances that are included in pouch assembly 24 should be non-reactive relative to both the fluid contained in sealed chamber 58 and the top and bottom surfaces themselves.

As can be seen in FIG. 1, as well as in FIGS. 10 and 11, outer seal 54 is of somewhat different configuration than inner seal 56. Specifically, outer seal 54 preferably comprises a substantially continuous seal around the circumference of the pouch assembly 24. Outer seal 54 is therefore preferably of uniform thickness and strength around that entire area, ensuring no one area is weaker than another.

Figure 5:
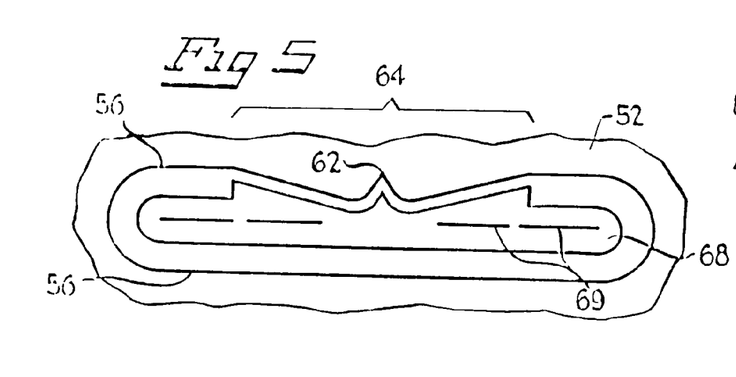
FIG. 5 of the drawings is a top view of the inner seal of the pouch apparatus.

On the other hand, inner seal 56, shown best in FIG. 5, comprises at least two different seal areas, and additionally comprises pinch point 62. In contrast with outer seal 54, inner seal 56 is deliberately formed with one region having a weaker connection than the other regions. For example, region one 64 of inner seal 56 is formed in substantially the same manner as outer seal 54. Region one 64 is of constant thickness and strength, leaving no one area within the region weaker than another. Region two 66 is similarly uniform. Region two 66 is formed from a different weld or sealing technique than region one 64, leaving the seal at region two 66 relatively weak when compared to the seal at region one 64 and in outer seal 54.

Region two 66 additionally comprises pinch point 62. Pinch point 62, as will be described in more detail below, acts as a focus for pressure applied to top surface 50 or bottom surface 52. If pressure is applied to the top or bottom surfaces, region two 66 of inner seal 56 will break first, specifically at pinch point 62, ensuring that fluid released from sealed fluid chamber 58 will be released in the desired direction.

Pinch point 62 is shown in FIG. 5 in its preferred formation, that of an inverted "V" shape. This "V" shape allows for the force applied to top surface 50 or bottom surface 52 to be directed specifically at one point. Any number of structures, however, will fulfill this purpose without deviating from the ideas embodied by this invention.

Pouch assembly 24 is shown in its preferred configuration, with one outer seal 54 and one inner seal 56, creating a sealed fluid chamber 58 therebetween. Additionally, the invention is shown as preferably having inner seal 56 comprising at least two seal regions, and a pinch point 62. In this configuration, outer seal 54 will be substantially uniform and continuous, while inner seal 56 is not.

It is additionally contemplated that other, similar configurations would provide the same or similar functions as are satisfied with the above preferred configuration. For example, outer seal 54 could have one or more regions of varying seal strength, and could have a pinch point 62 similar to inner seal 56. In that case, force applied to either top surface 50 or bottom surface 52 could pierce either inner seal 56 or outer seal 54. Similarly, inner seal 56 could instead be substantially uniform and continuous, ensuring it would remain intact while outer seal 54 was ruptured. Lastly, it is possible that there is no inner seal 56, with outer seal 54 running the length of the circumference of top surface 50 and bottom surface 52, forming a sealed fluid chamber 58 therein. All of these embodiments are contemplated by the present invention, and fall within the scope of the protection offered by this application.

As shown in FIG. 5, contained within inner seal 56 is release reservoir 68, in which are located fluid delivery slits 69. Fluid delivery slits 69 are located in and through top surface 50 or bottom surface 52 to provide a passageway through the two surfaces. The slits are located at or near the center of release reservoir 68, which is surrounded by inner seal 56. Since inner seal 56 marks the boundary of sealed fluid chamber 58, and sealed fluid chamber 58 is filled, preferably, with a fluid, the area surrounding inner seal 56 is raised in comparison with release reservoir 68. Therefore, release reservoir 68 acts as a valley into which the fluid released from sealed fluid chamber 58 will flow.

As can be seen in FIG. 1, pouch assembly 24 also includes sealant ring 67. Sealant ring 67 secures pouch assembly 24 within first recess 38 of tray assembly 22. When tray assembly 22 is opened for removal of electrode assembly 26, sealant ring 67 ensures pouch assembly 24 will remain with tray assembly 22, allowing unencumbered manipulation and use of electrode assembly 26 and separation pad 28. Sealant ring 67 is constructed from the same or similar material as pouch assembly 24, and is secured to tray assembly 22 using a non-reactive permanent adhesive. Therefore, upon sealing pouch to tray assembly 22, and upon subsequent release of fluid from pouch assembly 24, there are no side-reactions or byproducts created by the presence of sealant ring 67.

Figure 8:
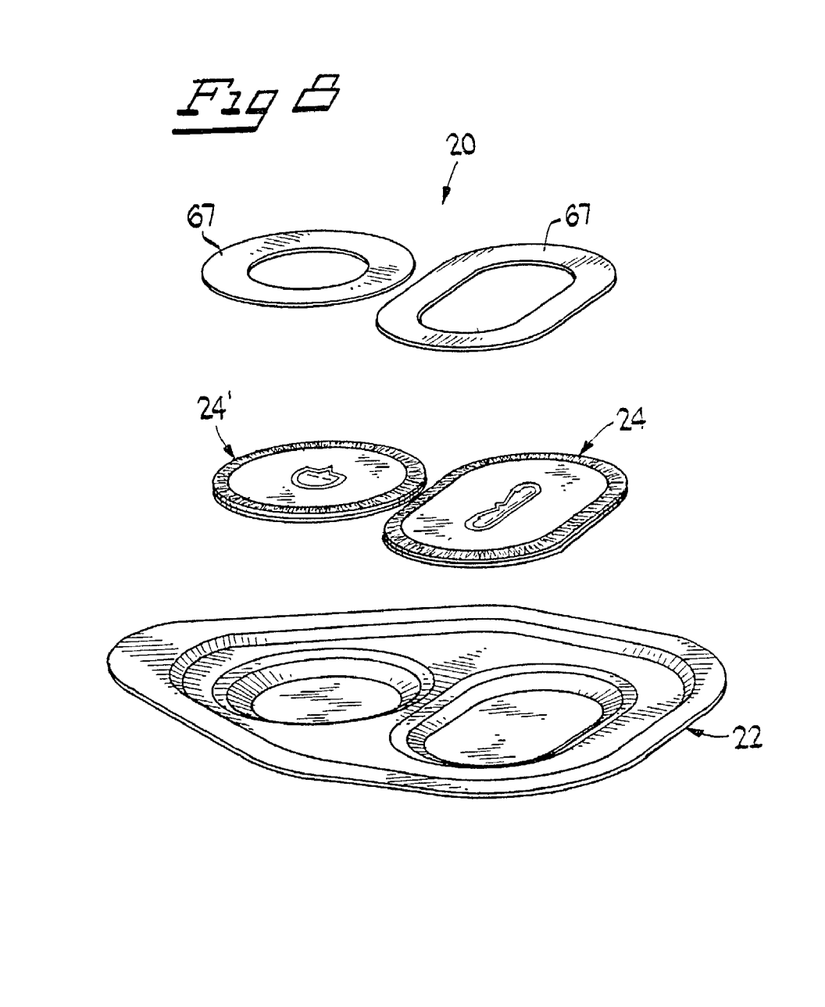
FIG. 8 of the drawings is an exploded view of the tray assembly and the pouch assembly with two pouch assemblies.

A preferred configuration of storage device 20 is shown in FIG. 8. As can be seen, storage device 20 comprises tray assembly 22, and at least two pouch assemblies 24, 24'. In this embodiment, the tray assembly 22 comprises much of the same structure as in FIG. 1, except that the layered structure described above is duplicated for a second pouch assembly 24'. As shown, at least two pouch assemblies 24, 24' are placed within the respective recesses of the tray assembly 22, and sealed therein with sealant ring 67. As will be discussed further below, the inclusion of two or more pouch assemblies 24, 24' within storage device 20, along with electrode assembly 26, provides for advantageous delivery of one or more fluids to electrode assembly 26 for later iontophoretic application.

Electrode assembly 26 is shown in FIG. 2 as comprising backing pad 70, wiring assembly 72, gum karaya pads 74, and medicament pad 76. Additionally, FIG. 2 shows the proper placement and inclusion of pouch assembly 24, discussed above, and separator pad 28, discussed below, within storage device 20 and adjacent electrode assembly 26. Electrode assembly 26, once properly contacted with the fluid contained in pouch assembly 24 or assemblies, can be removed from storage device 20, and applied to an arm, leg, or other surface of a patient for the iontophoretic delivery of a drug to that area.

Backing pad 70 is shown in FIG. 2 as a thin, flexible, water resistant base for wiring assembly 72, medicament pad 76, gum karaya pads 74 and separator pad 28. Backing pad 70 is preferably constructed from a thin portion of polyurethane material, formed in substantially the same shape as the imprint of the electrode assembly 26. The polyurethane additionally includes an adhesive on one side to adhere to the wiring assembly 72, and to portions of separator pad 28 and gum karaya pads 74, as will be discussed further below. The structures adhere to the exposed portions of backing pad 70 permanently, so that later manipulation and application of electrode assembly 26 to the surface of a skin is aided.

Wiring assembly 72 can be seen in FIG. 2 as comprising active electrode, 78, two passive electrodes 80, connecting wires 82, and lead wires 84. Active electrode 78 is depicted as a flat, oval-shaped metallic conductive element located directly under medicament pad 76. Active electrode 78 is connected through connecting wires 82 to lead wires 84 for later connection to a power source (not shown). Active electrode 78, after placing both it and the passive electrodes 80 on a patient and attaching a power source, provides an electric flux field across medicament pad 76 that drives an ionic medicament out of the pad and into the skin of a patient. In order to ensure complete coverage of medicament pad 76 by the electric flux field, active electrode 78 is formed so as to substantially correspond with the shape of medicament pad 76. Active electrode 78 may be constructed from any number of conducting materials as would be readily understood by those having ordinary skill in the art.

Passive electrodes 80 are shown as flat, semi-circular metallic conductive elements on opposite sides of active electrode 78. Passive electrodes 80 are connected to connecting wires 82, which in turn are connected to lead wires 84 for later connection to a power source. The passive electrodes 80 do not provide an electric flux to drive medicament into the skin of a patient. Instead, the passive electrodes 80 complete the electric circuit through the skin, providing for the transfer of electrons back to the power source. Passive electrodes 80 do have an electric field associated with them, however. The inclusion of two passive electrodes 80, and the placement of the electrodes on opposite sides of the active electrode 78, allows for this electric field to be spread out over a larger skin area. Since electric fields can cause irritation and discomfort when too concentrated, the spacing as well as the reduction in the size of the electrode enables higher flux through the active electrode 78 while reducing the occurrence of concentrated electric field irritations.

Passive electrodes 80 may be constructed from any number of conducting materials, similar to the active electrode 78. However, it is preferable to construct the passive electrodes 80 from a carbon conductive element.

Connecting wires 82 connect passive electrodes 80 to one lead wire 84', and active electrode 78 to the other lead wire 84". Lead wires 84 extend beyond the coverage provided by backing pad 70 in order to allow outside connection of electrode assembly 26 to a current source. Lead wires 84 and connecting wires 82 are conventional, as would be known in the art.

Figure 4:
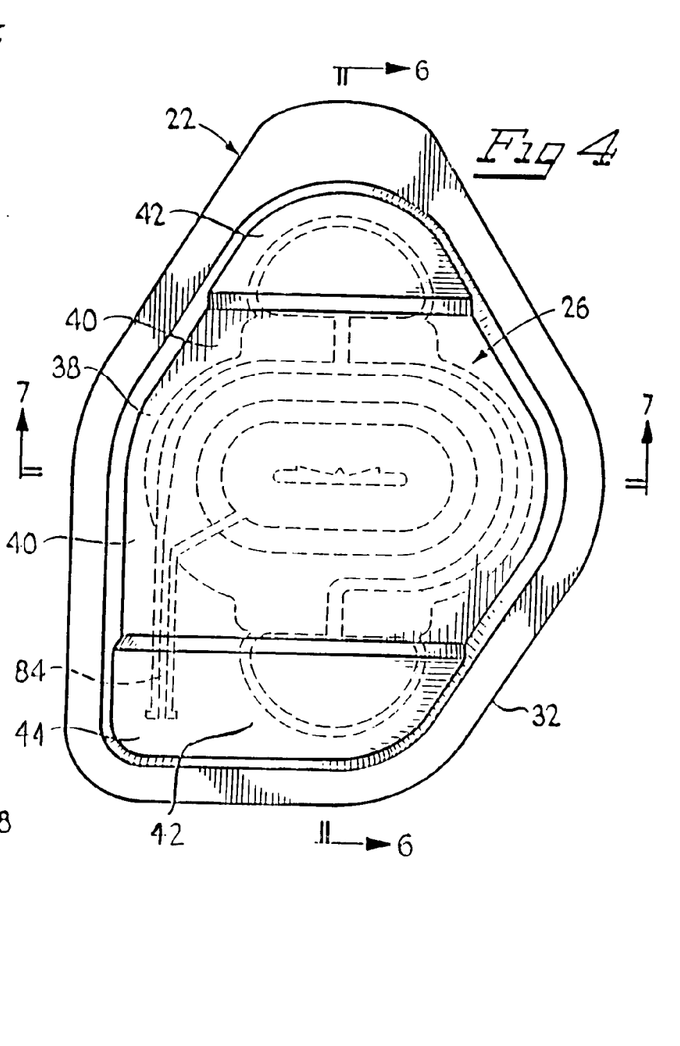
FIG. 4 of the drawings is a top plan view of the tray assembly and the electrode assembly.

The completed electrode assembly 26 can be seen in its proper orientation within tray assembly 22 in FIG. 4. Tray assembly 22 is shown with its three recessed areas, and also with extended area 44 of the third recess 42. Electrode assembly 26 fits properly in tray assembly 22 with medicament pad 76 and sealant member in second recess 40, and with the rest of electrode assembly 26, including lead wires 84, in third recess 42.

Gum karaya pads 74 are shown in FIG. 2 as semi-circular pads having the same or similar shape as passive electrodes 80. Gum karaya is a conductive, gummy substance that provides an electrical connection between passive electrodes 80 and the skin of a patient, while ensuring that passive electrodes 80 and the electrode assembly 26 will not move. There are other, similar, conductive adhesives that could also fulfill this function.

Medicament pad 76 is shown in a substantially oval shape, directly over and in line with active electrode 78. Medicament pad 76 is capable of receiving and retaining a medicament or other fluid for eventual dispersion through iontophoresis. Medicament pads 76 have been known in the art for some period of time, and may include such structures as a sponge, a disbursement pad, or a gel sponge. In each of these cases, medicament pad 76 may contain a medicament already, and merely be waiting for hydration from an outside source, or the medicament pad 76 can be dry.

The shape of medicament pad 76 can be altered to fit any desired application area. For example, if medicament pad 76 will be used to apply medicament to a circular-shaped area, medicament pad 76 can be altered to that shape. However, such alterations are a design choice that, preferably, incorporates the design of both active electrode 78 and pouch assembly 24. In other words, pouch assembly 24, medicament pad 76, and active electrode 78 are all preferably of the same cross-sectional shape. Therefore, the release of the fluid from pouch assembly 24 ensures complete coverage of medicament pad 76, and also complete flux of the medicament out of the pad once an electric field is applied.

Separator pad 28 is shown in FIG. 2 as a substantially oval structure having a cut-out 90 oval in its center. Additionally, separator pad 28 has wings 92 extending along its lateral sides. Cut-out 90 of separator pad 28 is formed so as to substantially correspond with the approximate shape of medicament pad 76. Separator pad 28 is adhered to connecting wires 82 of electrode assembly 26 and backing pad 70 of electrode assembly 26 in such a way as to maintain the spacing between separator pad 28, passive electrodes 80 and medicament pad 76 through usage of electrode assembly 26. The placement adjacent to, but spaced apart from medicament pad 76, creates moat region 94. Moat region 94, in turn, allows separator pad 28 to prevent any migration of medicament out of medicament pad 76 and active electrode 78 area toward passive electrodes 80, and similarly to prevent any electrical bleed through from active electrode 78 to passive electrodes 80. In both the cases of migrating medicament and electrical bleed through, separator pad 28 ensures that electrode assembly 26 will not short circuit itself, thus increasing the medicament flux across the skin of a patient.

In addition to preventing unwanted fluid and electrical transfers from medicament pad 76, it is similarly undesirable that fluid or other substance migrate from passive electrodes 80 and gum karaya pads 74 towards active electrode 78. Because of the nature of gum karaya, and as would be the problem with other, similar adhesives, there is an inherent fluidity to its makeup. Therefore, it is desirable to maintain the separation of the gum karaya and passive electrodes 80 from medicament pad 76. As such, separator pad 28 additionally includes wings 92 for maintaining the separation and integrity of gum karaya and medicament pad 76.

The above-mentioned functions of separator pad 28 presume that the properties of separator pad 28 allow it to act as both a fluid barrier and an electrical barrier. Separator pad 28 may be constructed from any number of materials capable of providing these functions. However, and preferably, the present invention includes separator pad 28 constructed from a polyurethane foam with a moderate thickness of approximately 1 mm.

In addition to the barrier functions of separator pad 28, separator pad 28 may also help the electrode assembly 26 to adhere to the skin of a patient. Since separator pad 28 is fixedly attached to wiring assembly 72 and backing pad 70 of electrode assembly 26, adding an adhesive to the exposed side of separator pad 28 enables the electrode assembly 26 to be securely affixed in a single position. However, it is important that the adhesive chosen be able to release without damaging the patient.

It is important to note that separator pad 28 is shown in FIG. 2 as comprising a complete oval surrounding medicament pad 76. It should also be noted, however, that portions or arcs of a pad may substantially serve the same purpose. Since fluid migration and electrical bleed is most undesirable in the direction of passive electrodes 80, separator pad 28 may comprise arcs or sections located between passive electrodes 80 and medicament pad 76. It is additionally contemplated that separator pad 28 could completely surround passive electrodes 80, leaving medicament pad 76 laterally open.

Figure 9:
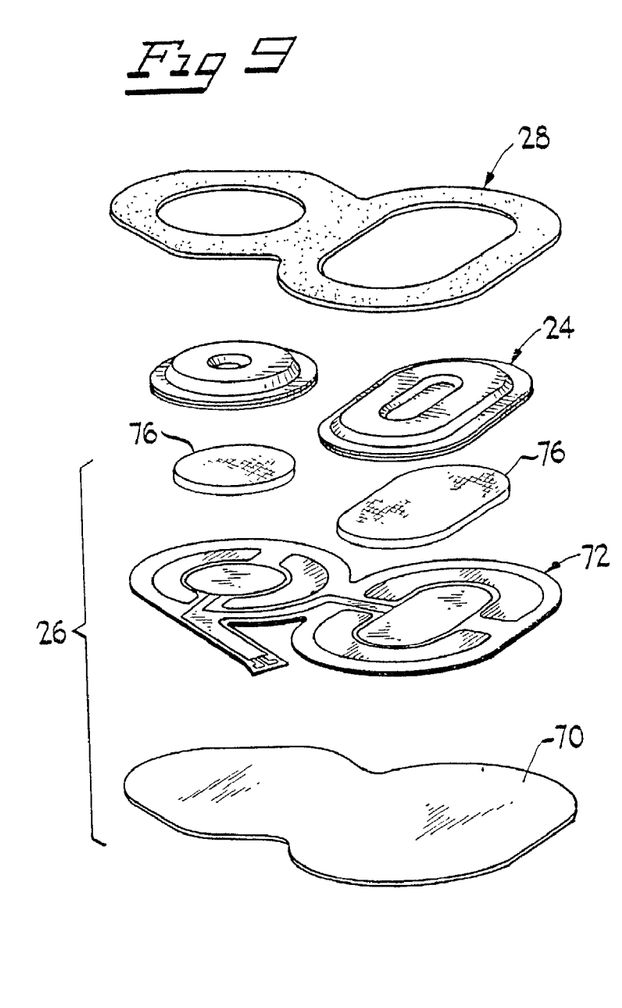
FIG. 9 of the drawings is an exploded view of the electrode assembly and the separator pad for use with two pouch assemblies.

Storage device 20 is properly assembled utilizing all of the above structures. First, tray assembly 22 is provided without cover 34. Next, pouch assembly 24 or assemblies (as seen in FIGS. 8 and 9) are inserted into tray assembly 22, and sealed therein with sealing ring. Next, electrode assembly 26 with separator pad 28 attached thereto is inserted into tray assembly 22, with medicament pad 76 being substantially aligned with pouch assembly 24. Electrode assembly 26 is essentially inserted upside-down, with medicament pad 76 contacting pouch assembly 24, wiring assembly 72 and gum karaya pads 74 at about the same level, and backing pad 70 on top, protecting the entire electrode assembly 26. Thereafter, cover 34 is attached to rim 32 of tray assembly 22, and storage assembly is ready for safe handling and shipping.

In operation, the already sealed storage device 20 is first removed from storage. Storage device 20 preferably already contains the desired components that are to be applied to the skin of a patient. Any number of pre-included fluids can be contained in the storage device 20, and specifically in pouch assembly 24. For example, pouch assembly 24 could contain an ionic medicament, such as is commonly used in iontophoretic drug delivery applications. Additionally, pouch assembly 24 could contain a hydrating compound which, when delivered to an appropriately drug-impregnated medicament pad 76, hydrates and activates a similar ionic medicament. In either case, the storage device 20 will have the necessary components preinstalled. Therefore, after removal of the storage device 20, an operator places storage device 20 with cover side down on a flat surface, or any other surface that will allow easy manipulation. Thereafter, the following steps are taken:

First, force is applied to deformable portion 36 of outer shell 30, deforming that portion of outer shell 30 towards and into top surface 50 of pouch assembly 24. Once deformable portion 36 and top surface 50 contact one another, force is transferred into top surface 50, towards bottom surface 52. This force compresses sealed fluid chamber 58, pushing fluid towards inner seal 56 of pouch assembly 24. Fluid ruptures region two 66 of inner seal 56, leaving region one 64 intact. Specifically, region two 66 is ruptured at pinch point 62, ensuring the directed release of the fluid from within sealed fluid chamber 58, out of pouch assembly 24.

Second, fluid flows out of sealed fluid chamber 58, through pinch point 62 of inner seal 56, and onto release reservoir 68. Release reservoir 68 receives the fluid, and directs it through fluid delivery slits 69 located at or near the center area of release reservoir 68. Fluid travels through fluid delivery slits, and onto medicament pad 76 located adjacent pouch assembly 24.

Depending upon what type of fluid is contained in pouch assembly 24, the contacting of the fluid with medicament pad 76 may merely saturate that pad 76 with an ionic medicament, as described above, or the fluid may hydrate an already impregnated medicament pad 76. Either way, the medicament contained in the medicament pad 76 or in the pouch assembly 24 does not become ready for application until the fluid is released from pouch assembly 24 and contacted with medicament pad 76.

Once medicament pad 76 is sufficiently hydrated, the operator removes cover 34 from rim 32 of tray assembly 22. This exposes backing pad 70 of electrode assembly 26. The operator thereafter removes electrode assembly 26 from tray assembly 22, leaving pouch assembly 24 contained within tray assembly 22, but removing electrode assembly 26 and sealing pad 28 with backing pad 70.

After removal, electrode assembly 26 is placed on the skin of a patient with gum karaya pads 74 and the adhesive portions of separator pad 28 facing down. Thereafter, power source (not shown) or controller (not shown) is attached to lead wires 84 in the appropriate order to create a medicament flux across the surface of a patient. For example, the positive side of a voltage drop should be applied to the active electrode if the hydrated medicament or the medicament delivered from the pouch assembly is a positively charged ionic species. Once affixed and connected, iontophoretic delivery of the medicament from the medicament pad 76 to the skin of a patient is achieved.

What is claimed is:

1. A fluid reservoir for use with a drug delivery device, the fluid reservoir comprising:
    a sealed fluid chamber including a top surface, a bottom surface, and a cavity there between, the cavity being at least partially defined by at least one seal and capable of holding a fluid therein;
    means for fracturing at least a portion of the at least one seal; and,
    means for controllably releasing the fluid from the cavity; wherein the at least one seal comprises at least a first attachment region; and,
    a second attachment region, wherein the first attachment region being weaker than the second attachment region, and
    a release reservoir adjacent the fluid reservoir having a means for directing released fluid to the release reservoir adjacent the fluid reservoir wherein the fluid direction means comprises at least one slit in the release reservoir.

2. The fluid reservoir of claim 1, wherein at least a portion of the top surface is deformable upon exertion of a force.

3. The fluid reservoir of claim 1 wherein the at least one seal comprising a pinch point.

4. The fluid reservoir of claim 1 wherein the first attachment region comprising a pinch point.

5. The fluid reservoir of claim 4, wherein at least a portion of the top surface is deformable upon exertion of a force.

6. The fluid reservoir of claim 1, wherein the fluid reservoir can be configured in numerous geometrical patterns, one of which is selected from the group consisting of circles, ovals, rectangles, and squares.

* * * * *